(12) United States Patent
Cunningham, Jr.

(10) Patent No.: US 9,370,444 B2
(45) Date of Patent: Jun. 21, 2016

(54) SUBCONJUNCTIVAL CONFORMER DEVICE AND USES THEREOF

(76) Inventor: Emmett T. Cunningham, Jr., Hillsborough, CA (US)

(*) Notice: Subject to any disclaimer, the term of this patent is extended or adjusted under 35 U.S.C. 154(b) by 0 days.

(21) Appl. No.: 13/272,030

(22) Filed: Oct. 12, 2011

(65) Prior Publication Data

US 2012/0089072 A1  Apr. 12, 2012

Related U.S. Application Data

(60) Provisional application No. 61/392,316, filed on Oct. 12, 2010.

(51) Int. Cl.
*A61F 9/00* (2006.01)
*A61F 9/007* (2006.01)

(52) U.S. Cl.
CPC .................................. *A61F 9/00781* (2013.01)

(58) Field of Classification Search
CPC .................................................... A61F 9/0017
See application file for complete search history.

(56) References Cited

U.S. PATENT DOCUMENTS

| | | | |
|---|---|---|---|
| 4,087,867 A | 5/1978 | Hickmann et al. | |
| 4,089,329 A | 5/1978 | Couvillon, Jr. et al. | |
| 4,402,681 A * | 9/1983 | Haas .................. | A61F 9/00781 604/175 |
| 4,554,918 A | 11/1985 | White | |
| 4,863,457 A | 9/1989 | Lee | |
| 4,922,913 A | 5/1990 | Waters, Jr. et al. | |
| 4,936,825 A | 6/1990 | Ungerleider | |
| 5,041,081 A | 8/1991 | Odrich | |
| 5,127,901 A | 7/1992 | Odrich | |
| 5,180,362 A | 1/1993 | Worst | |
| 5,300,020 A | 4/1994 | L'Esperance, Jr. | |
| 5,300,114 A | 4/1994 | Gwon et al. | |
| 5,326,345 A | 7/1994 | Price | |
| 5,370,607 A | 12/1994 | Memmen | |
| 5,433,701 A * | 7/1995 | Rubinstein ................ | 604/8 |
| 5,626,559 A * | 5/1997 | Solomon .................. | 604/9 |
| 6,142,969 A | 11/2000 | Nigam | |
| 6,168,575 B1 | 1/2001 | Soltanpour | |
| 6,443,893 B1 | 9/2002 | Shnakenberg et al. | |
| 6,468,283 B1 | 10/2002 | Richter et al. | |

(Continued)

FOREIGN PATENT DOCUMENTS

| | | |
|---|---|---|
| WO | WO-99/01063 | 1/1999 |
| WO | WO-01/21063 | 9/2001 |
| WO | WO-2007/136993 | 11/2007 |

OTHER PUBLICATIONS

Stedman's Medical Dictionary. New York: 2000. 27th Edition. pp. 1715. <http://stedmansonline.com/content.aspx?id=mlrS2100000862&termtype=t>.*

(Continued)

*Primary Examiner* — Philip R Wiest
*Assistant Examiner* — Sara Sass
(74) *Attorney, Agent, or Firm* — Wilson Sonsini Goodrich & Rosati

(57) ABSTRACT

The present invention provides a device for use in an eye with elevated intraocular pressure or glaucoma, the device comprising a subconjunctival conformer shaped to conform to the eye wall and a fluid director that directs or facilitates the flow of intraocular fluid out of the eye and into the subconjunctival or retrobulbar space. The present invention also provides a method of lowering intraocular pressure using the device of the present invention.

40 Claims, 3 Drawing Sheets

(56) References Cited

U.S. PATENT DOCUMENTS

| | | |
|---|---|---|
| 6,579,235 B1 | 6/2003 | Abita et al. |
| 6,638,976 B2 | 10/2003 | Gamache et al. |
| 6,682,500 B2 | 1/2004 | Soltanpour et al. |
| 6,713,081 B2 | 3/2004 | Robinson et al. |
| 6,730,056 B1 | 5/2004 | Ghaem et al. |
| 6,796,942 B1 | 9/2004 | Kreiner et al. |
| 6,881,197 B1 | 4/2005 | Nigam |
| 6,962,573 B1 | 11/2005 | Wilcox |
| 7,247,702 B2 | 7/2007 | Gardner et al. |
| 8,093,212 B2 | 1/2012 | Gardner et al. |
| 8,206,333 B2 | 6/2012 | Schmidt et al. |
| 8,308,701 B2 | 11/2012 | Horvath et al. |
| 2003/0175324 A1 | 9/2003 | Robinson et al. |
| 2003/0229303 A1 | 12/2003 | Haffner |
| 2004/0170665 A1 | 9/2004 | Donovan |
| 2004/0180075 A1 | 9/2004 | Robinson et al. |
| 2004/0193095 A1 | 9/2004 | Shadduck |
| 2004/0254517 A1 | 12/2004 | Quiroz-Mercado et al. |
| 2005/0048099 A1 | 3/2005 | Shiah et al. |
| 2005/0119601 A9 | 6/2005 | Lynch et al. |
| 2005/0119636 A1* | 6/2005 | Haffner et al. ............... 604/500 |
| 2005/0182350 A1 | 8/2005 | Nigam |
| 2007/0190111 A1 | 8/2007 | Robinson et al. |
| 2007/0248646 A1 | 10/2007 | Hafezi-Moghadam et al. |
| 2007/0293807 A1* | 12/2007 | Lynch et al. ............... 604/8 |
| 2008/0058704 A1 | 3/2008 | Hee et al. |
| 2008/0107712 A1 | 5/2008 | Shiah et al. |
| 2008/0112923 A1 | 5/2008 | Hughes et al. |
| 2008/0125691 A1 | 5/2008 | Yaron et al. |
| 2008/0131484 A1 | 6/2008 | Robinson et al. |
| 2008/0145403 A1 | 6/2008 | Spada et al. |
| 2008/0228127 A1* | 9/2008 | Burns et al. ............... 604/9 |
| 2009/0214538 A1 | 8/2009 | Fung et al. |
| 2009/0326432 A1 | 12/2009 | Schmidt et al. |
| 2010/0100104 A1 | 4/2010 | Yu et al. |
| 2010/0121249 A1 | 5/2010 | Yu et al. |
| 2010/0234791 A1 | 9/2010 | Lynch et al. |
| 2010/0272777 A1 | 10/2010 | Robinson et al. |
| 2011/0071454 A1 | 3/2011 | Dos Santos et al. |
| 2011/0071456 A1 | 3/2011 | Rickard et al. |
| 2011/0071458 A1 | 3/2011 | Rickard et al. |
| 2011/0071459 A1 | 3/2011 | Rickard et al. |
| 2011/0251201 A1 | 10/2011 | Huang et al. |
| 2011/0280829 A1 | 11/2011 | David et al. |
| 2011/0309546 A1 | 12/2011 | Shiah et al. |
| 2012/0089073 A1 | 4/2012 | Cunningham |

OTHER PUBLICATIONS

Hong et al., "Glaucoma drainage devices: a Systematic Literature Review and Current Controversies," Survey of Ophthalmology, vol. 50, No. 1, Jan./Feb., pp. 48-60 2005.

Wolbarsht et al., "A scleral buckle pressure gauge for continuous monitoring of intraocular pressure," International Ophthalmology, vol. 3, No. 1, Dec. 1980.

Kitco. "Gauge to Inches to Millimeters Conversion Table." <http://www.kitco.com/jewelry/gauge-inch-mm.html>. Oct. 12, 1999.

U.S. Appl. No. 13/272,062 Office Action mailed Feb. 14, 2014.

* cited by examiner

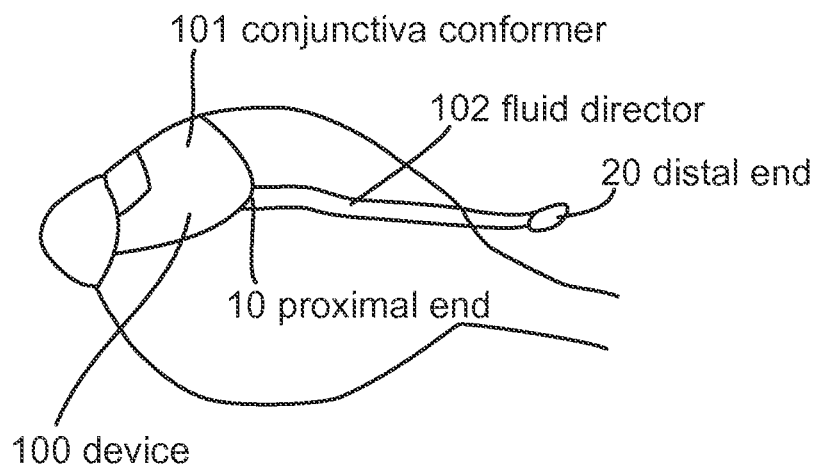
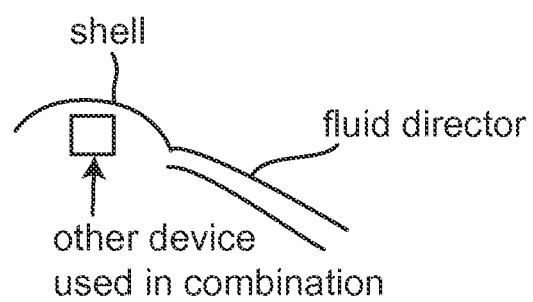

SUBCONJUNCTIVAL CONFORMER DEVICE AND USES THEREOF

CROSS REFERENCE

This application claims priority to U.S. Provisional Application 61/392,316, filed Oct. 12, 2010, the contents of which are incorporated herein in their entirety.

BACKGROUND OF THE INVENTION

Glaucoma is a major cause of blindness worldwide. The blindness that results from glaucoma can involve both central and peripheral vision and can have a major impact on an individual's ability to lead an independent and productive life. Pathophysiologically, glaucoma is an optic neuropathy (a disorder of the optic nerve) observed most typically in the setting of an elevated intraocular pressure. Dramatic and/or prolonged increases in intraocular pressure cause changes in the appearance ("cupping" or "excavation") and function ("scotomas" or "blind spots" in the visual field) of the optic nerve. If the pressure remains high enough for a long enough period of time, total, irreversible vision loss occurs. High intraocular pressure results from an imbalance in intraocular fluid production versus outflow. Glaucoma surgeries, also referred to as filtering procedures, are designed to improve intraocular fluid balance by augmenting fluid outflow, thereby lowering intraocular pressure.

The most commonly performed filtering procedure for treating an eye with an elevated intraocular pressure is a trabeculectomy. During a trabeculectomy, the conjunctiva or the transparent tissue that covers the sclera is incised and reflected to expose the sclera at and immediately posterior to the corneoslceral junction or limbus. A partial thickness scleral flap is then made and dissected forward into the cornea. The anterior chamber is entered beneath the scleral flap by excising a section of deep sclera and together with the underlying trabecular meshwork. The scleral flap then sutured back into place so as to regulate flow of intraocular fluid to the subconjunctival space. The potential subconjunctival space surrounding and posterior to the scleral flap is then dissected so as to facilitate subconjunctival flow of fluid prior to suturing the conjunctival incision tightly closed. Post-operatively, the aqueous fluid passes through the sclerectomy/trabeculectomy, beneath the scleral flap, and into the expanded subconjunctival space. The fluid then is either absorbed through blood vessels in the conjunctiva or traverses across the conjunctiva to mix with the tear film.

Trabeculectomy is associated with many problems. Fibroblasts that are present in the subconjunctival space are induced by the trauma of surgery to proliferate and migrate, thus promoting scar formation and closure of the subconjunctival outflow path. Of eyes that have an initially successful trabeculectomy, eighty percent will fail from scarring within three to five years after surgery. Failure from scarring is particularly common in children and young adults. To minimize fibrosis, surgeons often apply antifibrotic agents, such as mitomycin C (MMC) and 5-fluorouracil (5-FU), to the scleral flap and surrounding subconjunctival space at the time of surgery. The use of these agents has increased the success rate of trabeculectomy, but also has increased the prevalence of overfiltration and hypotony, or excessively low intraocular pressure (usually less than 6.0 mmHg). Prolonged hypotony is associated with retinal distortion, loss of vision, and ultimately, loss of structural integrity of the eye, Trabeculectomy creates a pathway for intraocular fluid to escape the eye. At the same time, however, trabeculectomy creates a potential pathway for bacteria that normally colonize the surface of the eye and eyelids to enter the eye—causing a severe intraocular infection known as endophthalmitis. In addition to subconjunctival scarring, hypotony and endophthalmitis, there are other recognized complications of trabeculectomy. The conjunctiva over the sclerectomy/trabeculectomy site, know as a "bleb," can tear, producing excessive filtration and profound hypotony. In addition, large anteriorly located blebs can be irritating, can disrupt the normal tear film, leading to blurred vision, and can make it difficult for patients to wear contact lenses. All of the complications of trabeculectomy stem from poorly directed flow intraocular fluid once it enters the subconjunctival space.

Many glaucoma drainage devices have been used in the management of resistant glaucoma as an alternative to trabeculectomy. These include use of shunting devices, which include the Molteno device, the Ahmed device, the Kruppin device and the Baerveldt device. Other shunting devices include the Schocket implant, the Ex-Press R50, and the AGV silicon tube. A publication entitled, Glaucoma Drainage Devices: A Systematic Literature Review and Current Controversies provides a systematic review of the literature and outlines the current issues involving different glaucoma drainage devices and their design, overall surgical success and complications following glaucoma drainage device insertion (e.g., see Hong, et al, A Systematic Literature Review and Current Controversies; Survey of Ophthalmology; Volume 50, Number 1, January-February 2005).

These known devices suffer from certain shortcomings. One problem with known glaucoma drainage devices is that the location of their insertion can cause damage to the anterior chamber structures, such as the cornea, the iris, or the intraocular lens. Another problem with such devices is related to complications caused by their occlusion by fibrosis and/or infection. Another problem with the know devices is their associated difficulty is establishing and regulating a sufficient amount of flow that would allow intraocular pressure to be titrated following the procedure. Another known problem of such devices is the problems associated with double vision, limitation of eye movement and so on that can be encountered with shunting devices with external reservoirs.

There is therefore a need for a device that can be used in combination with trabeculectomy or other intraocular drainage devices that can optimize fluid flow from inside the eye to the subconjunctival space and, in some embodiments, posteriorly to the retrobulbar space.

SUMMARY OF THE INVENTION

In one aspect, the present invention provides a device for use in an eye with elevated intraocular pressure or glaucoma, the device comprising a subconjunctival conformer shaped to conform to the eye wall, adapted and configured to create a permanent subconjunctival space, and a fluid director adapted and configured to facilitate a flow of intraocular fluid to a subconjunctival space or a retrobulbar space.

In some embodiments, the fluid director has a tubular shape. In some embodiments, the fluid director has one or more lumens adapted and configured for diverting intraocular fluid from anterior or posterior chambers or vitreous cavity to subconjunctival space at the pars plana or retrobulbar space. In some embodiments, the device of the present invention further comprises more than one fluid director. In some embodiments, the device is implantable. In some embodiments, the device is constructed of a bioerodible material. The bioerodible material can be polyester, polyorthoester, polyanhydride, polylactic, polyglycolic, polyvinyl acid polymer, polytetrafluoroethylene, fluorinated polymer, flexible fused silica, polyolefin, polyamide, parylene, composite of carbohydrates, polysaccharides, collagen, or a combination thereof. In other embodiments, the device is constructed of a non-bioerodible material. The non-bioerodible material can be titanium, stainless steel, cobalt-chromium-nickle-molybdenum-iron alloy, nickel-titanium alloy, tantalum, metal, silicone, silicone polymer, polyurethane, plastic, acrylic polymer, or any combination thereof. The bioerodible and non-bioerodible materials can be smooth, textured, or corrugated. In some embodiments, the device is constructed of multiple polymeric layers of bioerodible and/or non-bioerodible materials. In some embodiments, the surface of the device is porous with a mesh or matrix design. In some embodiments, the device of the present invention is adapted and configured to be placed between conjunctiva and scleral surface of the eye.

In some embodiments, the subject device further comprises one or more drug-eluting coatings. The coating can minimize inflammation, scarring, fibrosis, and/or infection. In some embodiments, the drug is an anti-inflammatory agent, anti-proliferative agent, anti-scarring agent, anti-microbial agent, antiseptics, intraocular pressure lowering agent, or vitreolytic agent. In some embodiments, the anti-inflammatory agent is selected from the group consisting of corticosteroids, immunosuppressive agents, non-steroidal anti-inflammatory drugs, anti-inflammatory proteins, peptides, or nucleic acids, and combinations thereof In some embodiments, the anti-proliferative agent is selected from the group consisting of a corticosteroid, an immunosuppressive agent, mitomycin, 5-fluorouracil, heparin, anti-proliferative proteins, peptides, or nucleic acids and combinations thereof In some embodiments, the anti-scarring agent is mitomycin or 5-flurouracil. In some embodiments, the anti-microbial agent is selected from the group consisting of antibiotics, antivirals, antifungals, and antiparasitics. In some embodiments, the intraocular pressure lowing agent is selected from the group consisting of an adrenergic agonist, cholinergic agonist, beta-blocker, carbonic anhydrase inhibitor, prostaglandin analogue, and alpha-adrenergic agonist. In some embodiments, the vitreolytic agent is selected from the group consisting of a dispase, urea, collagenase, hyaluronidase, plasmin, microplasmin, chondroitinase, a protease, and combinations thereof.

In some embodiments, the device of the present invention further comprises a securing structure adapted and configured for suturing and fixating the device to the eye wall. The securing structure can be a ring or a flange-like structure. The flange-like structure can be sized and shaped to fit on the surface of the sclera at the pars plana so as to prevent the device from dislocating or migrating. In some embodiments, the subject device is used in combination with eye surgery, for example, trabeculectomy. In some embodiments, the subject device is adapted and configured to be placed in connection with one or more filtering or shunting devices to enhance and/or direct intraocular fluid flow from anterior or posterior chambers or vitreous cavity to subconjunctival space or retrobulbar space. Examples of shunt devices include but are not limited to Ahmed valve, Molteno valve, and Krupin slit valve. In some embodiments, the device is adapted and configured to be placed over, below, around, or adjacent to the filtering or shunting device to minimize scarring, fibrosis, inflammation, and/or infection, and facilitate the egress of intraocular fluid from the filtering or shunting device. In some embodiments, the device is used in combination with another device for monitoring intraocular pressure over a period of time. In some embodiments, intraocular fluid is drained to the subconjunctival space or retrobulbar space at a sufficient flow rate to reduce intraocular pressure. In one example, the subject device is used for treating glaucoma.

In another aspect, the present invention provides a method of lowering intraocular pressure, the method comprising introducing into an eye the subject device of the present invention as described herein, and directing intraocular fluid from anterior or posterior chambers or vitreous cavity to the subconjunctival space or retrobulbar space. In some embodiments, a potential space between conjunctiva and scleral surface of the eye is maintained. In some embodiments, the method of the present invention further comprises an eye surgery, such as trabeculectomy. In some embodiments, the subject method further comprises placing a shunt device to the subconjunctival space or the retrobulbar space.

INCORPORATION BY REFERENCE

All publications, patents, and patent applications mentioned in this specification are herein incorporated by reference to the same extent as if each individual publication, patent, or patent application is specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows a side view of an eye where the device 100 in accordance with the embodiments of the present invention is implanted.

FIG. 2B shows that the subject device can be used in combination with another filtering or shunting device.

DETAILED DESCRIPTION OF THE INVENTION

Disclosed herein are devices for use in an eye with elevated intraocular pressure or glaucoma, the device comprising a subconjunctival conformer comprising: a bowl-shaped shell comprising a proximal rim configured to contact a scleral surface at the eye wall upon positioning said bowl-shaped shell between the sclera and conjunctiva, and a distal surface configured to contact the conjunctiva, thereby creating a permanent subconjunctival space in an interior of the bowl-shaped shell; and a fluid director configured to and placed to facilitate a flow of intraocular fluid from the interior of the bowl-shaped shell to a subconjunctival space, or retrobulbar space.

Throughout this application, various publications, patents and published patent applications are cited. The disclosures of these publications, patents and published patent applications referenced in this application are hereby incorporated by reference in their entirety into the present disclosure. Citation herein by Applicant of a publication, patent, or published patent application is not an admission by Applicant of said publication, patent, or published patent application as prior art.

Figure 1:
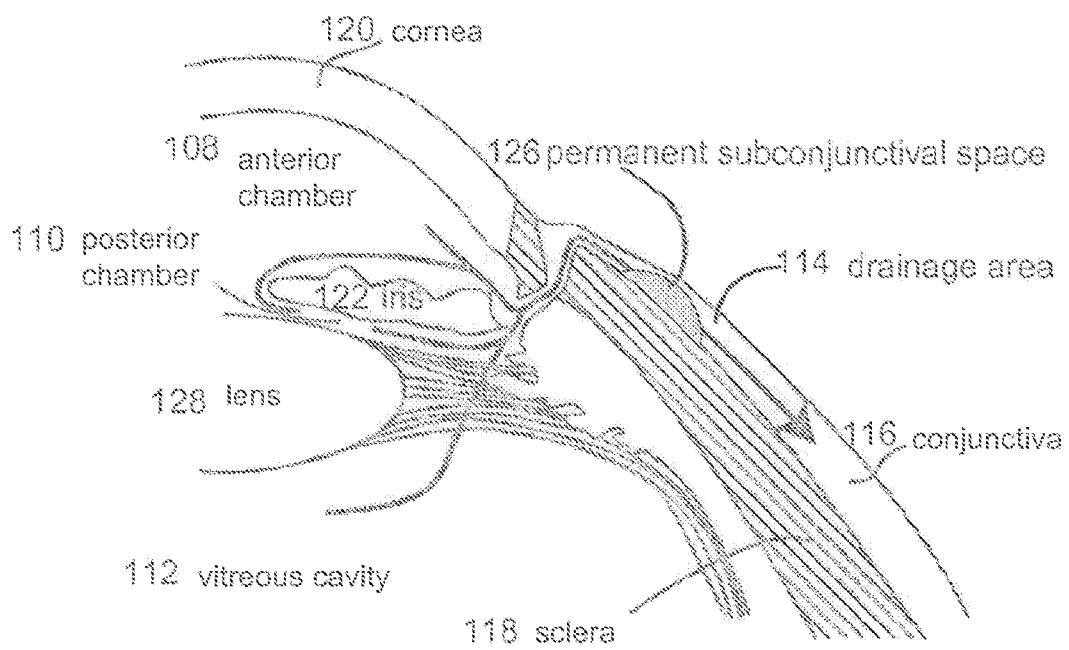
FIG. 1 shows the subconjunctival space where the device of the present invention can be implanted.

The present invention is directed to a glaucoma drainage device. In some embodiments, the device 100 comprises a subconjunctival conformer 101 shaped to conform to the eye wall, to maintain a subconjunctival space, and to a fluid director 102 that directs or facilitates the flow of intraocular fluid from either the anterior chamber or posterior chamber or vitreous cavity of the eye to the subconjunctival space (drainage area, conjunctiva) or the retrobulbar space. FIG. 1 shows the subconjunctival space where the device of the present invention can be implanted through the sclera near the cornea. While the iris may appear detached in FIG. 1, in fact this merely shows a cross section where the device may be placed to form a path (shown by the arrow having starting points in the anterior chamber, posterior chamber through a path through the iris, or around the iris, or from the vitreous cavity) for the drainage or flow of intraocular fluid into the conjunctiva (subconjunctiva space, retrobulbar space).

In some embodiments, the fluid director has a tubular shape. FIG. 2A shows a side view of an eye where the device 100 in accordance with the embodiments of the present invention is implanted. The subconjunctival conformer 101 and the fluid director 102 are shown. FIG. 2B shows that the subject device can be used in combination with another filtering or shunting device. The fluid director can have one or more lumens for diverting intraocular fluid from anterior or posterior chambers or vitreous cavity to subconjunctival space at the pars plana or retrobulbar space. In some embodiments, the device further comprises more than one fluid director. The device of the present invention can be implantable. It can be constructed of a bioerodible material or a non-bioerodible material or a combination of more than one bioerodible or non-bioerodible material. In some embodiments, the device of the present invention further comprises one or more drug-eluting coatings to minimize inflammation, scarring, fibrosis, and/or infection. The drug can be an anti-inflammatory agent, anti-proliferative agent, anti-scarring agent, anti-microbial agent, intraocular pressure lowering agent, or vitreolytic agent, or a combination thereof. In some embodiments, the device of the present invention can also elute chemical antiseptics or antifibrotics. The antiseptics that can be used in the device of the present invention include but are not limited to alcohols, quaternary ammonium compounds, boric acid, chlorhexidine gluconate, hydrogen peroxide, iodine, mercurochrome, octenidine dihydrochloride, phenol (carbolic acid) compounds, sodium chloride, sodium hypochlorite, calcium hypochlorite, and sodium bicarbonate. Examples of the antifibrotic agents include but are not limited to 5-fluorouracil and mitomycin C.

Figure 3:
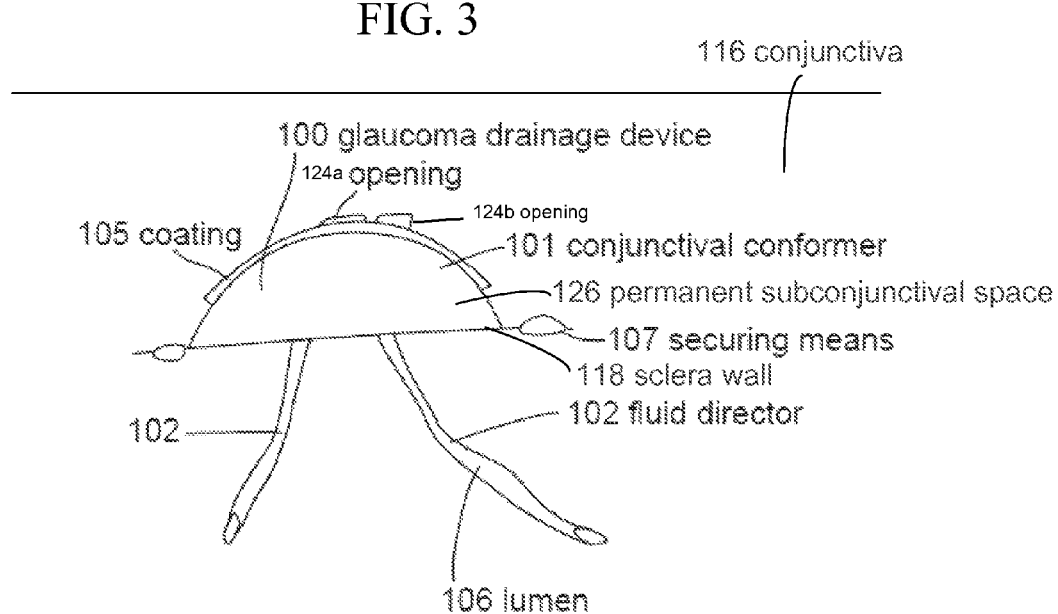
FIG. 3 shows details corresponding to the external surface of the device having a securing structure 107 for securing the implant in place; a drug-eluting coating 105 and multiple openings on the surface of the device.

In some embodiments, the device further comprises securing structure. FIG. 3 shows details corresponding to the external surface of the device having a securing structure 107 for securing the implant in place; a drug-eluting coating 105 and multiple openings on the surface of the device. The subconjunctival conformer 101 and two fluid directors 102 are shown each having a lumen for directing fluid from the drainage device openings 124a, 124b out of the anterior chamber or posterior chamber or vitreous cavity of the eye to the subconjunctival space (drainage area, conjunctiva or the retrobulbar space. In some embodiments, the securing structure 107 is a suture that connects the device to the sclera (or other eye structure). In some embodiments, the securing structure is another securing structure and comprises a ring or a flange. In some embodiments In some embodiments, the securing structure comprises a ring or a flange-like structure, for suturing and fixating the device to the eye wall. In some embodiments, the flange-like structure is sized and shaped to fit on the surface of the sclera at the pars plana so as to prevent the device from dislocating or migrating. The location at the pars plana allows for the drainage of fluid from the eye without allowing the drainage device to touch the anterior chamber structures (e.g., iris and the cornea) or lens, as it is known that this touch is a major cause of complications and shunt failures.

The subject device can be used in combination with an eye surgery, for example, trabeculectomy. The device can also be placed in connection with one or more filtering or shunting devices to help maintain the subconjunctival space and enhance and/or direct intraocular fluid flow from anterior or posterior chambers or vitreous cavity to the subconjunctival space or the retrobulbar space. In some embodiments, the present invention helps maintain the subconjunctival space, which tends to scar closed, thereby reducing the scarring caused by trabeculectomy or other intraocular fluid drainage devices. In some embodiments, the device of the present invention assists in the regulation of fluid flow out of the eye and into the subconjunctival or retrobulbar space. In some embodiments, the fluid directors have microperforations to limit posterior flow. Thus, in one example, the subject device can be used for treating glaucoma.

In another aspect, the present invention provides a method of lowering intraocular pressure, the method comprising introducing into an eye the subject device disclosed herein, and directing intraocular fluid from anterior or posterior chambers or vitreous cavity to the subconjunctival space or the retrobulbar space.

Device

In some embodiments, the device of the present invention 100 comprises a subconjunctival conformer 101. The subconjunctival conformer is shaped so as to conform to the eye wall and so as to have no sharp edges that can cause irritation to the eye and or perforate the conjunctiva. In some embodiments, the device of the present invention 100 utilizes a wide range of subconjunctival conformers that are used to conform to the conjunctival sac fornices. In some embodiments, they are positioned closely to the socket contour and fill the depths of the fornices without stretching them. In some embodiments, the subconjunctival conformer is perforated, i.e. can have one or more ports to facilitate post-operative management or the insertion of post-operative medications. In some embodiments, the device of the present invention 100 is used after insertion of certain eye implants, which include but are not limited to various filtering or shunt devices, for example, Molteno, Baerveldt, Ahmed glaucoma valve, Krupin slit valve, Shocket, the OptiMed, White shunt pump, the Joseph implants, and the Express shunt. The subconjunctival conformer 101 can be of various sizes, for example, 20 mm, 22 mm, 24 mm, 26 mm and 28 mm in diameter.

In some embodiments, the device of the present invention 100 comprises a fluid director 102 which itself conforms to the sclera surface, having a central lumen 106 and a securing structure 107 for fixating the device to the eye wall. In some embodiments, the lumen 106 can be single patent lumen of appropriate size (e.g., approximately between 20 and 40 gauge) to permit the normalization of the intraocular pressure. In some embodiments, the lumen 106 of the fluid director 102 can be used for diverting intraocular fluid from the anterior or posterior chambers or vitreous cavity to the subconjunctival space at the pars plana or to the retrobulbar space at the back of the eye. In some embodiments, more than one fluid director is used to direct intraocular fluid from the anterior or posterior chambers or vitreous cavity to the subconjunctival space or the retrobulbar space. The one or more fluid director can contain a mechanism whereby insertion of a dilating or canalizing instrument could dilate or open the lumen 106 of the fluid director 102. One such mechanism includes an adjustable diaphragm. Such an adjustable diaphragm can be controlled mechanically, or could use an electrical, magnetic and/or heat sensitive activation mechanism. The one or more fluid directors can include one or more flow regulating mechanisms. Such flow regulating mechanisms can include carbon-based, silicon-based, or other polymer-based materials forming nanotubes, capillary tubes, collimated holes, and combinations thereof. In some embodiments, the one or more fluid directors can include biological mechanoproteins, including, but not limited to, forisomes, that could be used to regulate fluid flow. The present invention contemplates many different configurations of the fluid director, provided that each of the fluid directors assists in channeling intraocular fluid from the anterior or posterior chambers or vitreous cavity to the subconjunctival space or the retrobulbar space, such as by providing a lumen, trough, wick or capillary action. For example, the fluid director can have a fully enclosed lumen, a partially enclosed lumen, or a trough-like channel that is at least partially open.

In some embodiments, the device is an implant. The device of the present invention is well fixated, that does not incite an immune or foreign body reaction, that incites minimal inflammation, that has no sharp edges, and that can be easily placed into and removed from the eye. The device 100 can be made of a material that is compatible with the tissues and fluids with which it is in contact. The device can be constructed of any number of bioerodible or non-bioerodible materials. The terms "bioerodible" "bioabsorbable" and "biodegradable" are herein used interchangeably. In some embodiments, the device is not absorbed, corroded, or otherwise structurally compromised during its in situ use. Moreover, the eye tissues and the aqueous remain non-detrimentally affected by the presence of the device 100. Examples of bioerodible materials include but are not limited to polyester, polyorthoester, polyanhydride, polylactic, polyglycolic, polyvinyl acid polymer, polytetrafluoroethylene, fluorinated polymer, flexible fused silica, polyolefin, polyamide, parylene, composite of carbohydrates, polysaccharides, collagen, and combination thereof. Examples of non-bioerodible materials include but are not limited to titanium, stainless steel, cobalt-chromium-nickle-molybdenum-iron alloy, nickel-titanium alloy, tantalum, metal, silicone, silicone polymer, polyurethane, plastic, acrylic polymer, or any combination thereof. In some embodiments, the device can be made of a biodegradable material selected from the group consisting of poly(lactic acid), polyethylene-vinyl acetate, poly(lactic-co-glycolic acid), poly(D,L-lactide), poly(D,L-lactide-co-trimethylene carbonate), poly(caprolactone), and poly(glycolic acid). In some embodiments, the device 100 is constructed of multiple polymeric layers of any bioerodible and/or non-bioerodible materials. In some embodiments, the material of the device 100 is smooth, textured, or corrugated. The device can be constructed as either porous or solid. In some embodiments, the internal intraocular surface of the device can have multiple openings or surface corrugations to reduce the risk of occlusion by the vitreous. In some embodiments, the surface of the device 100 is porous with a mesh or matrix design.

In some embodiments, the device of the present invention comprises a securing structure 107 for suturing or fixating the device onto the eye wall. Examples of the securing structures include but are not limited to a ring or a flange-like structure. In some embodiments, the subconjunctival conformer 101 of the implant device 100 includes a flange-like structure 107 that is larger than the fluid director portion 102 and the flange-like structure is sized and shaped to fit on the surface of the retina at the pars plana so as to prevent the implant device 100 from dislocating or migrating. There can be one or more securing structures, including but not limited to rings or flanges, for attaching the device on the eye wall.

In one example, the proximal portion 10 of the device has a flange-like structure 107 extending therefrom to maintain the position of the device in the subconjunctival space. In alternative embodiments, such a flange-like structure can extend from distal portion 20 of the device to assist in stabilization of the implant within the retrobulbar space. The flange-like structure facilitates implantation and proper placement of the device, as the proximal portion can be advanced into the anterior chamber and then pulled back into place until it contacts the edge of the anterior chamber. The flange-like structure can be fabricated by a simple thickening of the material of construction of the device, e.g. silicon, at the desired site on the proximal portion, or can be made of another material disclosed herein. Additionally, the flange-like structure can be fabricated by removal of excess material. The flange-like structure can extend from the proximal portion in virtually any functional shape, such as in a rounded or barbed fashion. Therefore, the flange-like structure can extend circumferentially around the proximal portion, or only in one or more directions therefrom. The invention contemplates many other configurations of the securing structure, including a plurality of teeth extending from the proximal portion. It is understood that the securing structure, for example, a flange can extend in any direction in any shape and size which facilitates implantation or anchoring of the device. The device should be at least capable of permitting the flow of aqueous humor at the estimated normal production rate of about 2.5 microliters per minute. The securing structure as well as optionally the remainder of the device can be constructed on a textured, grooved, or porous material in order to facilitate the growth of cells, such as fibroblasts, to stabilize the implant device from movement. Preferably, the extreme tips of the proximal and distal ends of the device are produced to avoid the attraction of new tissues, such as fibroblasts, which can grow at the surgical site and impede the flow of aqueous therethrough.

In some embodiments, the implant device 100 has one or more coatings 105. The coating 105 can have a drug-eluting property. In some embodiments, the drug-eluting coating can be an anti-inflammatory agent, anti-proliferative agent, anti-scarring agent, anti-microbial agent, intraocular pressure lowering agent, or vitreolytic agent. The anti-inflammatory agent can be selected from the group consisting of corticosteroids, immunosuppressive agents such as tacrolimus, sirolimus, and methotrexate, non-steroidal anti-inflammatory drugs, anti-inflammatory proteins, peptides, or nucleic acids, and combinations thereof. The anti-proliferative agent can be selected from the group consisting of a corticosteroid, an immunosuppressive agent, mitomycin, 5-fluorouracil, heparin, anti-proliferative proteins, peptides, or nucleic acids and combinations thereof The anti-scarring agent can be mitomycin or 5-flurouracil. The anti-microbial agent can be selected from the group consisting of antiseptics, antibiotics, antivirals, antifungals, and antiparasitics.

The intraocular pressure lowing agent can be selected from the group consisting of an adrenergic agonist, cholinergic agonist, beta-blocker, carbonic anhydrase inhibitor, prostaglandin analogue, and alpha-adrenergic agonist. The vitreolytic agent can be selected from the group consisting of a dispase, urea, collagenase, hyaluronidase, plasmin, microplasmin, chondroitinase, a protease, and combinations thereof. Examples of other agents that can be eluted from the device of the present invention include but are not limited to anthracycline, doxorubicin, mitoxanthrone, fluoropyrimidine, 5-fluorouracil, a folic acid antagonist, methotrexate, podophylotoxin, etoposide, camptothecin, hydroxyurea, a platinum complex, cisplatin, anti-thrombotic agent, visualization agent, or echogenic material. In some embodiments, where growth is desired for stability, certain growth factors can be present, whereas at places where obstructions are to be avoided, certain antifibrotic agents can be present, such as 5-fluourouracil or mitomycin. In some embodiments, the device is more generally provided with coatings that are antibiotic, anti-inflammatory, or carboxylic anhydrase inhibitors. Agents that facilitate the degradation of collagen within the trabecular meshwork can also be employed.

In some embodiments, the device is adapted for delivering the drug or agent locally to tissue proximate to the device. In some embodiments, the drug is released in the vicinity of the device 100 after deployment of the device. In some embodiments, the drug is released in effective concentrations from the device over a period ranging from the time of deployment of the device to about 1 year. In some embodiments, the drug is released in effective concentrations from the device at a constant rate, an increasing rate or a decreasing rate. In some embodiments, the device comprises more than one coating wherein the drugs eluted from the first coating and the second coating are the same or different. The coating 105 can partially or completely cover the device 100. The coating can be uniform, non-uniform, discontinuous, or patterned.

Where the pharmaceutical delivery system of the present invention comprises a drug eluting polymer matrix, the drug eluting polymer can be conveniently made from siloxane copolymer, such as a fluorinated side-chain polysiloxane optionally polymerized with a comonomer such as methyl methacrylate, N,N-dimethylacrylamide, acrylamide, N-methylacrylamide, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, N-vinylpyrrolidione and hydroxybutyl methacrylate. By varying the concentration of the hydrophobic siloxane backbone, the polar —$CF_2H$ tail and any comonomer(s), if used, the hydrophobic/hydrophilic balance and hence the pharmaceutical agent release characteristics of the polymer coating can be controlled.

In some embodiments, the device of the present invention can be used in connection with eye surgery, for example, trabeculectomy. In some embodiments, the device of the present invention can be used in connection with any of the existing filtering/shunting devices including but not limited to the Molteno device, the Ahmed device, the Kruppin device, the Baerveldt device, the Schocket implant, the Ex-Press R50, and the AGV silicon tube. For example, there exist a number of aqueous shunt devices, such as U.S. Pat. No. 4,936,825 (providing a tubular shunt from the anterior chamber to the corneal surface for the treatment of glaucoma), U.S. Pat. No. 5,127,901 (directed to a transscleral shunt from the anterior chamber to the subconjunctival space), U.S. Pat. No. 5,180,362 (teaching a helical steel implant that is placed to provide drainage from the anterior chamber to the subconjunctival space), and U.S. Pat. No. 5,433,701 (generally teaching shunting from the anterior chamber to the scleral or subconjunctival spaces), which are all incorporated by reference herein. The device 100 of the present invention can be placed over, below, around, or adjacent to the filtering or shunting device to minimize scarring, fibrosis, inflammation, and/or infection, and facilitate the egress of intraocular fluid from the filtering or shunting device.

In some embodiments, the device of the present invention can be either constructed with or used together with devices that are intended to monitor intraocular pressure over an extended period of time. For example, a noninvasive, continuous monitoring device for measuring intraocular pressure without interference with vision or normal activity of the patient is disclosed in U.S. Pat. No. 4,089,329. A miniature, planar-faced pressure transducer is fixed in a protruding section of a compliant hydrogel ring which has been tooled to conform to the spherical surface of the sclera. The hydrogel ring is placed noninvasively under the eyelids within the conjunctival cul-de-sac, the transducer being located in the lower temporal quadrant. Applanation of the sclera against the planar surface of the transducer results as a consequence of pressure from the separated tissues. Intraocular pressure readings are based on the variations in resistance in the strain gage elements of the transducer caused by the applied stress to the transducer diaphragm. Other examples of intraocular pressure sensor or monitoring devices that can be used in conjunction with the device of the present invention include devices disclosed in U.S. Pat. Nos. 4,922,913 and 6,579,235, and International Application No. PCT/US2007/068536, and in Myron L. Wolbarsht et al. International Ophthalmology Volume 3, Number 1/December, 1980, all of which are herein incorporated by reference in their entirety.

The implant device 100 in accordance with the embodiments of the present invention offer many advantages over known devices. One of the known problems with existing shunt devices and trabeculectomy is scarring and hypotony (low post-op pressure due to over filtration of the filter). The implant device in accordance with the embodiments of the present invention addresses these known problems by incorporating drug eluting technology, either intrinsically or through the use of a coating material. Anti-inflammatory, anti-microbial, and/or anti-scarring agent can be applied to the eye via the implant device. The use of a drug-eluting coating 105 reduces the risk of occlusion by fibrosis and/or infection. In addition, most known shunt devices treat the eye by diverting fluid from the anterior chamber to the subconjunctival space. The device in accordance with the embodiments of the present invention differs from the known devices by maintaining the subconjunctival space, allowing for optimal intraocular fluid drainage. The device of the present invention also helps direct and distribute the intraocular fluid more evenly from the drainage site. One advantageous feature of the present invention is directed towards the placement of the device at the pars plana. The placement of the device at the pars plana reduces the potential for damage to, and occlusion by, anterior chamber structures.

The device of the present invention can be a part of a kit that includes the canalization probes of varying sizes that can be used to open or reopen the lumen of the fluid director as is needed to establish and/or maintain intraocular pressure. In such case, the probes could have tapered tips to facilitate passage posteriorly within the subconjunctival space.

Uses

In another aspect, the present invention provides a method of lowering intraocular pressure, the method comprising introducing into an eye a device of the present invention, and directing intraocular fluid from anterior or posterior chambers or vitreous cavity to the subconjunctival space or the retrobulbar space. In some embodiments, the intraocular fluid is drained to the subconjunctival space or retrobulbar space at a sufficient flow rate to reduce intraocular pressure. In some embodiments, the size and shape of the subconjunctival conformer can be selected and/or adjusted to optimize intraocular pressure regulation. In some embodiments, the flow rate of the aqueous humor is below about 2.5 microliters per minute. In some embodiments, the flow rate of the aqueous humor is sufficient to maintain eye pressure above 6.0 mmHg In some embodiments, the aqueous humor is produced by the eye at a rate that is about the same as the flow rate of aqueous humor through the fluid director 102. In some embodiments, the flow rate in the presence of the device of the present invention maintains eye pressure between approximately 15 mmHg and 21 mmHg. In some embodiments, the intraocular fluid is drained at a sufficient flow rate to reduce build-up of the fluid in the anterior or posterior chamber or the vitreous cavity without hypotony.

In some embodiments, the device is used for treating an eye condition with high intraocular pressure. For example, the device can be used for treating glaucoma. Glaucoma can be divided roughly into two main categories, "open angle" or chronic glaucoma and "closed angle" or acute glaucoma. The device of the present invention can be used to treat both forms of glaucoma. The device can be used in conjunction with any existing surgery for treating glaucoma, for example, trabeculectomy. In some embodiments, a potential space between conjunctiva and scleral surface of the eye is maintained. In some embodiments, the subject method of the present invention further comprises trabeculectomy. In some embodiments, the subject method further comprises placing a shunt device to the subconjunctival space or the retrobulbar space in connection with the device 100 of the present invention.

In some embodiments, the device is used for a direct release of pharmaceutical preparations into ocular tissues. The pharmaceuticals can be compounded within the device, form a coating on the device. The device when coated or loaded with a slow-release substance can have prolonged effects on local tissue surrounding the device. The slow-release delivery can be designed such that an effective amount of substance is released over a desired duration. "Substance" or "therapeutic substance", as used herein, is defined as any therapeutic or active drug that can stop, mitigate, slow-down or reverse undesired disease processes. Any known drug therapy for glaucoma can be utilized. A listing of some known drug therapies for treating glaucoma that can be used in the present invention are disclosed in U.S. Published Patent Application No. 20030229303, which is herein incorporated by reference in its entirety.

Examples of the drug or agent that can be used in the present invention to reduce inflammation, scarring, fibrosis, infection, or enhance the therapeutic function or enhance healing include but are not limited to brefeldin A, a histamine receptor antagonist, an alpha adrenergic receptor antagonist, an anti-psychotic compound, a CaM kinase II inhibitor, a G protein agonist, an antibiotic selected from the group consisting of apigenin, ampicillin sodium salt, puromycin, an anti-microbial agent, a DNA topoisomerase inhibitor, a thromboxane A2 receptor inhibitor, a D2 dopamine receptor antagonist, a Peptidyl-Prolyl Cis/Trans Isomerase Inhibitor, a dopamine antagonist, an anesthetic compound, a clotting factor, a lysyl hydrolase inhibitor, a muscarinic receptor inhibitor, a superoxide anion generator, a steroid, an anti-proliferative agent, a diuretic, an anti-coagulant, a cyclic GMP agonist, an adenylate cyclase agonist, an antioxidant, a nitric oxide synthase inhibitor, an antineoplastic agent, a DNA synthesis inhibitor, a DNA alkylating agent, a DNA methylation inhibitor, a NSAID agent, a peptidylglycine alpha-hydroxylating monooxygenase inhibitor, an MEK1/MEK 2 inhibitor, a NO synthase inhibitor, a retinoic acid receptor antagonist, an ACE inhibitor, a glycosylation inhibitor, an intracellular calcium influx inhibitor, an anti-emetic agent, an acetylcholinesterase inhibitor, an ALK-5 receptor antagonist, a RAR/RXT antagonist, an eIF-2a inhibitor, an S-adenosyl-L-homocysteine hydrolase inhibitor, an estrogen agonist, a serotonin receptor inhibitor, an antithrombotic agent, a tryptase inhibitor, a pesticide, a bone mineralization promoter, a bisphosphonate compound selected from risedronate and an analogue or derivative thereof, an anti-inflammatory compound, a DNA methylation promoter, an anti-spasmodic agent, a protein synthesis inhibitor, an α-glucosidase inhibitor, a calcium channel blocker, a pyruvate dehydrogenase activator, a prostaglandin inhibitor, a sodium channel inhibitor, a serine protease inhibitor, an intracellular calcium flux inhibitor, a JAK2 inhibitor, an androgen inhibitor, an aromatase inhibitor, an anti-viral agent, a 5-HT inhibitor, an FXR antagonist, an actin polymerization and stabilization promoter, an AX0R12 agonist, an angiotensin II receptor agonist, a platelet aggregation inhibitor, a CB1/CB2 receptor agonist, a norepinephrine reuptake inhibitor, a selective serotonin reuptake inhibitor, a reducing agent, and a immuno-modulator selected from Bay 11-7085, (–)-arctigenin, idazoxan hydrochloride, an angiogenesis inhibitor, an apoptosis antagonist, an apoptosis activator, a beta 1 integrin antagonist, a beta tubulin inhibitor, a blocker of enzyme production in Hepatitis C, a Bruton's tyrosine kinase inhibitor, a calcineurin inhibitor, a caspase 3 inhibitor, a CC chemokine receptor antagonist, a cell cycle inhibitor, a cathepsin B inhibitor, a cathepsin K inhibitor, a cathepsin L inhibitor, a CD40 antagonist, a chemokine receptor antagonist, a chymase inhibitor, a collagenase antagonist, a CXCR antagonist, a cyclin dependent kinase inhibitor, a cyclooxygenase 1 inhibitor, a DHFR inhibitor, a cual integrin inhibitor, an elastase inhibitor, an elongation factor-1 alpha inhibitor, an endothelial growth factor antagonist, an endothelial growth factor receptor kinase inhibitor, an endotoxin antagonist, an epothilone and tubulin binder, an estrogen receptor antagonist, an FGF inhibitor, a farnexyi transferase inhibitor, a farnesyltransferase inhibitor, an FLT-3 kinase inhibitor, an FGF receptor kinase inhibitor, a fibrinogen antagonist, a histone deacetylase inhibitor, an HMGCoA reductase inhibitor, an ICAM inhibitor, an IL, ICE, and IRAK antagonist, an IL-2 inhibitor, an immunosuppressant, an inosine monophosphate inhibitor, an integrin antagonist, an interleukin antagonist, an inhibitor of type III receptor tyrosine kinase, an irreversible inhibitor of enzyme methionine aminopeptidase type 2, an isozyme selective delta protein kinase C inhibitor, a JAK3 enzyme inhibitor, a JNK inhibitor, a kinase inhibitor, a kinesin antagonist, a leukotriene inhibitor and antagonist, a MAP kinase inhibitor, a matrix metalloproteinase inhibitor, an MCP-CCR2 inhibitor, an mTOR inhibitor, an mTOR kinase inhibitor, a microtubule inhibitor, an MIF inhibitor, a neurokinin antagonist, an NF kappa B inhibitor, a nitric oxide agonist, an ornithine decarboxylase inhibitor, a p38 MAP kinase inhibitor, a palmitoyl-protein thioesterase inhibitor, a PDGF receptor kinase inhibitor, a peroxisome proliferator-activated receptor (PPAR) agonist, a phosphatase inhibitor, a phosphodiesterase inhibitor, a PKC inhibitor, a platelet activating factor antagonist, a prolyl hydroxylase inhibitor, a polymorphonuclear neutrophil inhibitor, protein kinase B inhibitor, protein kinase C stimulant, purine nucleoside analogue, a purineoreceptor P2X antagonist, a Raf kinase inhibitor, reversible inhibitor of ErbBi and ErbB2, ribonucleoside triphosphate reductase inhibitor, an SDF-1 antagonist, a sheddase inhibitor, an SRC inhibitor, a stromelysin inhibitor, an Syk kinase inhibitor, a telomerase inhibitor, a TGF beta inhibitor, a TNF-alpha antagonist or TACE inhibitor, a tumor necrosis factor antagonist, a Toll receptor inhibitor, a tubulin antagonist, a protein tyrosine kinase inhibitor, a VEGF inhibitor, a vitamin D receptor agonist, a retinoic acid receptor antagonist, a heat shock protein 90 antagonist, a steroid, a cell cycle inhibitor, a histone deacetylase inhibitor, an anti-microbial agent, an intracellular calcium flux inhibitor, an\microtubule inhibitor, an HMGCoA reductase inhibitor, an actin polymerization and stabilization promoter, a tyrosine kinase inhibitor, a TGF beta inhibitor, a TNF-alpha antagonist, a TACE inhibitor, a calcineurin inhibitor, a peptidyl-prolyl cis/trans isomerase inhibitor, an apoptosis activator, an antimetabolite and antineoplastic agent, a TGF beta inhibitor, a DNA methylation promoter, and a PKC inhibitor ZD-6474, AP-23573, synthadotin, S-0885, aplidine, ixabepilone, IDN-5390, SB-2723005, ABT-518, combretastatin, anecortave acetate, SB-715992, temsirolimus, adalimumab, erucylphosphocholine, alphastatin, etanercept, humicade, gefitinib, isotretinoin, radicicol, clobetasol propionate, homoharringtonine, trichostatin A, brefeldin A, thapsigargin, dolastatin 15, cerivastatin, jasplakinolide, herbimycin A, pirfenidone, vinorelbine, 17-DMAG, tacrolimus, loteprednol etabonate, juglone, prednisolone, puromycin, 3-BAABE, cladribine, mannose-6-phosphate, 5-azacytidine, Ly333531 (ruboxistaurin), and simvastatin.

In some embodiments, the drug eluting coating can include at least one therapeutic agent selected from the group consisting of a gene, a growth factor, and an enzyme.

EXAMPLE

Results of Preclinical Study in Animal Eyes
Study Device
A study in 16 swine is performed using a device of the present invention. The device is implanted in one eye of each animal and the non-implanted eye serves as a control.
Surgical Procedure
For each animal, the periocular area of the study eye is prepped (eyelash trimming and betadine). The animal is then anesthesized using isofluorane. Under sterile conditions, a lid speculum is used to open the eyelids. An operating microscope is swung into place. A peripheral corneal bridle suture is placed to rotate the eye and expose the superior nasal limbus. A fornix-based conjunctival incision is made in the sclera and hemostasis ensured with bipolar cautery. A partial-thickness triangular scleral flap that measured 4×4 mm is made at the limbus and dissected anteriorly into clear cornea. A second, deeper flap is created at the base of the first flap, and dissected anteriorly to unroof the porcine equivalent of Schlemm's canal. The plane of the deeper flap then is angled anteriorly to create a corneoscleral shelf. A viscoelastic agent (hyaluronate and chondroitin sulfate) is instilled into the subconjunctival space using a viscocanalostomy cannula. The anterior chamber is entered through the corneoscleral shelf and a viscoelastic agent instilled into the anterior chamber. The proximal (radial) portion of the device is inserted into the anterior chamber through the corneoscleral shelf. The scleral flaps are tightly closed with 10-0 nylon sutures and the knots buried. The conjunctiva is closed with absorbable suture. The bridle suture is removed. Subconjuctival garamycin and decadron are instilled interiorly. The eye is dressed with tobramycin-decadron ointment. The animal is allowed to awaken and returned to the boarding area.

In each case, the surgical endpoints are achieved. The subconjunctival space is accurately located and unroofed in 16 of 16 eyes and the device is successfully implanted without complication. Neither ocular structures nor the device are damaged during implantation. The surgical site is adequately closed without difficulty. During the procedure there is no observable touching between the device and the corneal endothelium, no collapse of the anterior chamber, no anterior chamber bleeding requiring ishout, no tearing of the iris, and no touching between the device and the iris. All animals tolerated the surgery and anesthesia well.

Clinical Observations
All animals tolerate the implant procedure well. No animal demonstrates post-operative pain or discomfort as evidenced by rubbing, decreased eating or sleeping. No sight-threatening complications occur due to implanting the device. Specifically, there is no chronic inflammatory reaction to the device, erosion of surrounding tissues, choroidal detachment or hemorrhage, retinal detachment, or infection.

The swine included in this study are normal animals without glaucoma. At baseline, the average intraocular pressures of the right and left eyes are equivalent. At 3 months post-operatively, the intraocular pressure in the study eye with the device is 14% lower than the contralateral (control) eye (n=16 animals).

Demonstration of in vivo Fluid Flow
At 3 months, two devices are explanted from two eyes for pressure-flow testing. In these eyes, a fornix-based conjunctival incision is made over the scleral flap. The scleral flap is gently loosened from the surrounding tissue and dissected forward to unroof the subconjunctival space. The device is identified within the space and the distal portions of the device are removed from the space, leaving the proximal portion within the anterior chamber. At this point, aqueous fluid is observed to flow through the fluid director from the anterior chamber out of the fluid director to the retrobulbar space, demonstrating in vivo flow through the device.

Similar in vivo experiments can be performed in other animals including but not limited to rabbit, dog and primate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:
1. A device for use in an eye with elevated intraocular pressure or glaucoma, the device comprising a subconjunctival conformer comprising:
   a. a bowl-shaped shell, configured to be placed over or in proximity to a drainage site, comprising: a proximal rim configured to contact a scleral surface at the eye wall upon positioning said bowl-shaped shell between the sclera and conjunctiva, and a distal convex outer surface configured to contact the conjunctiva, thereby creating and/or maintaining a permanent subconjunctival space in an interior of the bowl-shaped shell; and
   b. a fluid director having a proximal opening and a distal opening, and wherein the fluid director:
      i. is configured to conform to the scleral surface;
      ii. extends from a drainage opening on the distal convex outer surface of the bowl shaped shell, wherein a wall of the bowl-shaped shell is continuous with a wall of the fluid director, and the proximal opening is physically continuous with the drainage opening on the distal convex outer surface of the bowl-shaped shell and the distal opening is positioned outside the bowl-shaped shell; and iii. is configured to receive and direct subconjunctival flow of intraocular fluid so that the direction of flow is from the interior of the bowl-shaped shell through the opening on the distal convex outer surface of the bowl-shaped shell, through the proximal opening in the fluid director, and through the distal opening in the fluid director, thus directing the intraocular fluid away from the drainage site to a subconjunctival space or a retrobulbar space.

2. The device of claim 1, wherein the fluid director has a tubular shape.

3. The device of claim 1, wherein the fluid director has a lumen adapted and configured for diverting subconjunctival flow of intraocular fluid from anterior or posterior chambers or the vitreous cavity to the subconjunctival space at a pars plana or retrobulbar space.

4. The device of claim 1, wherein the device is implantable.

5. The device of claim 1, wherein the device is constructed of a bioerodible material.

6. The device of claim 5, wherein the bioerodible material is selected from the group consisting of polyester, polyorthoester, polyanhydride, polylactic, polyglycolic, polyvinyl acid polymer, polytetrafluoroethylene, fluorinated polymer, flexible fused silica, polyolefin, polyamide, parylene, composite of carbohydrates, polysaccharides, collagen, and combination thereof.

7. The device of claim 1, wherein the device is constructed of a non-bioerodible material.

8. The device of claim 7, wherein the non-bioerodible material is selected from the group consisting of titanium, stainless steel, cobalt-chromium-nickle-molybdenum-iron alloy, nickel-titanium alloy, tantalum, metal, silicone, silicone polymer, polyurethane, plastic, acrylic polymer, or any combination thereof.

9. The device of claim 5 or 7, wherein the material is smooth, textured, or corrugated.

10. The device of claim 1, wherein the device is constructed of multiple polymeric layers of bioerodible and/or non-bioerodible materials.

11. The device of claim 1, wherein a surface of the device is porous with a mesh or matrix design.

12. The device of claim 1, wherein the device is adapted and configured to be placed between the conjunctiva and the scleral surface of the eye.

13. The device of claim 1, further comprising a drug-eluting coating.

14. The device of claim 13, wherein the coating minimizes inflammation, scarring, fibrosis, and/or infection.

15. The device of claim 13, wherein the drug is an anti-inflammatory agent, anti-proliferative agent, anti-scarring agent, anti-microbial agent, antiseptic, intraocular pressure lowing agent, or vitreolytic agent.

16. The device of claim 15, wherein the anti-inflammatory agent is selected from the group consisting of corticosteroids, immunosuppressive agents, non-steroidal anti-inflammatory drugs, anti-inflammatory proteins, peptides, or nucleic acids, and combinations thereof.

17. The device of claim 15, wherein the anti-proliferative agent is selected from the group consisting of a corticosteroid, an immunosuppressive agent, mitomycin, 5-fluorouracil, heparin, anti-proliferative proteins, peptides, or nucleic acids and combinations thereof.

18. The device of claim 15, wherein the anti-scarring agent is mitomycin or 5-flurouracil.

19. The device of claim 15, wherein the anti-microbial agent is selected from the group consisting of antibiotics, antivirals, antifungals, and antiparasitics.

20. The device of claim 15, wherein the intraocular pressure lowing agent is selected from the group consisting of an adrenergic agonist, cholinergic agonist, beta-blocker, carbonic anhydrase inhibitor, prostaglandin analogue, and alpha-adrenergic agonist.

21. The device of claim 15, wherein the vitreolytic agent is selected from the group consisting of a dispase, urea, collagenase, hyaluronidase, plasmin, microplasmin, chondroitinase, a protease, and combinations thereof.

22. The device of claim 1, further comprising a securing structure adapted and configured for suturing and fixating the device to the sclera.

23. The device of claim 22, wherein the securing structure is selected from the group consisting of: a ring, a plurality of teeth, and a flange-like structure.

24. The device of claim 23, wherein the flange-like structure is sized and shaped to fit on the surface of the sclera at the pars plana so as to prevent the device from dislocating or migrating.

25. The device of claim 1, wherein the device is used in combination with eye surgery.

26. The device of claim 25, wherein the eye surgery is trabeculectomy.

27. The device of claim 1, wherein the device is adapted and configured to be placed in connection with one or more filtering or shunting devices to enhance and/or direct subconjunctival flow of intraocular fluid from the anterior or posterior chambers or the vitreous cavity of the eye to the subconjunctival space or the retrobulbar space.

28. The device of claim 27, wherein the shunt device is an Ahmed valve, Molteno valve, or Krupin slit valve.

29. The device of claim 27, wherein the device is placed over, below, around, or adjacent to the filtering or shunting device to minimize scarring, fibrosis, inflammation, and/or infection, and facilitate the egress of intraocular fluid from the filtering or shunting device.

30. The device of claim 1, wherein the device is used in combination with another device for monitoring intraocular pressure over a period of time.

31. The device of claim 1, wherein subconjunctival flow of intraocular fluid drains to the subconjunctival space or retrobulbar space at a sufficient flow rate to reduce intraocular pressure.

32. The device of claim 1, wherein the device is used for treating glaucoma.

33. A method of lowering intraocular pressure, the method comprising:
a. introducing into an eye with a drainage site a device that comprises a subconjunctival conformer, wherein the subconjunctival conformer comprises:
i. a bowl-shaped shell, wherein the bowl-shaped shell comprises a proximal rim, a distal convex outer surface, and an interior of the bowl-shaped shell; and
ii. a fluid director having a proximal opening and a distal opening that is configured to conform to the scleral surface and extends from a drainage opening on the distal convex outer surface of the bowl-shaped shell, wherein the proximal opening is physically continuous with the drainage opening on the convex outer surface of the bowl-shaped shell and the distal opening is positioned outside of the bowl-shaped shell;
b. positioning the bowl-shaped shell over or in proximity to the drainage site;

c. contacting a scleral surface with the proximal rim of the bowl-shaped shell;
d. contacting the conjunctiva with the distal surface of the bowl-shaped shell; and
e. directing subconjunctival flow of intraocular fluid from the interior of the bowl-shaped shell through the fluid director to a subconjunctival space or a retrobulbar space, wherein the subconjunctival flow is directed from the interior of the bowl-shaped shell, through the proximal opening of the fluid director, and through the distal opening of the fluid director.

34. The method of claim 33, wherein the device creates and/or maintains a permanent subconjunctival space between the conjunctiva and the scleral surface.

35. The method of claim 33, further comprising an eye surgery trabeculectomy, wherein the eye surgery trabeculectomy produces the drainage site.

36. The method of claim 33, further comprising placing the device in connection with a filtering and/or shunt device.

37. The method of claim 36, further comprising placing the filtering and/or shunt device to enhance and/or direct intraocular fluid from a region of the eye selected from an anterior chamber, posterior chamber and a vitreous cavity.

38. The method of claim 36, further comprising placing the filtering and/or shunt device to enhance and/or direct subconjunctival flow of intraocular fluid to the subconjunctival space or the retrobulbar space.

39. The method of claim 36, wherein the bowl-shaped shell is placed over, below, around, or adjacent to the shunting device.

40. The device of claim 1, wherein the subconjunctival space is at the pars plana.

* * * * *